United States Patent [19]
Mega et al.

[11] Patent Number: 5,172,183
[45] Date of Patent: Dec. 15, 1992

[54] GLOW DISCHARGE ATOMIC EMISSION SPECTROSCOPY AND APPARATUS THEREOF

[75] Inventors: Tetsuya Mega; Michio Katayama; Masao Yokoi; Yasuko Furunushi, all of Chiba, Japan

[73] Assignee: Kawasaki Steel Corporation, Hyogo, Japan

[21] Appl. No.: 670,584

[22] Filed: Mar. 18, 1991

[30] Foreign Application Priority Data

Mar. 19, 1990 [JP] Japan .................................. 2-67364

[51] Int. Cl.$^5$ ............................................ G01N 21/66
[52] U.S. Cl. ..................................... 356/311; 356/313
[58] Field of Search ........................ 356/311, 313, 314

[56] References Cited
FOREIGN PATENT DOCUMENTS

| | | |
|---|---|---|
| 49-21680 | 6/1974 | Japan . |
| 55-33241 | 8/1980 | Japan . |
| 161851 | 9/1983 | Japan .................. 356/311 |
| 145949 | 6/1988 | Japan .................. 356/313 |
| 210751 | 9/1988 | Japan .................. 356/311 |

OTHER PUBLICATIONS

Waitlevertch et al., Applied Spectroscopy, vol. 30, No. 5, pp. 510–515 Sep.–Oct. 1976.
Iron and Steel (Japan), vol. 69 (1983), No. 10, pp. 1344–1349, Ohashi et al., "Surface Analysis of Steels by Modified Glow Discharge Spectrometry".

*Primary Examiner*—F. L. Evans
*Attorney, Agent, or Firm*—Oliff & Berridge

[57] ABSTRACT

An improved glow discharge atomic emission spectroscopy method and apparatus is offered in which the introduction of a rare gas into a glow discharge tube is temporarily cut off and after the inside of the glow discharge tube is maintained at a higher degree of vacuum, a preliminary discharge is executed to remove adsorbed or extraneous substances on the specimen surface, and then the analysis of the specimen surface is performed. The method and the apparatus described in the above are suitable for quick and simple analysis of the uppermost surface layer of a solid specimen in the direction of depth.

6 Claims, 9 Drawing Sheets

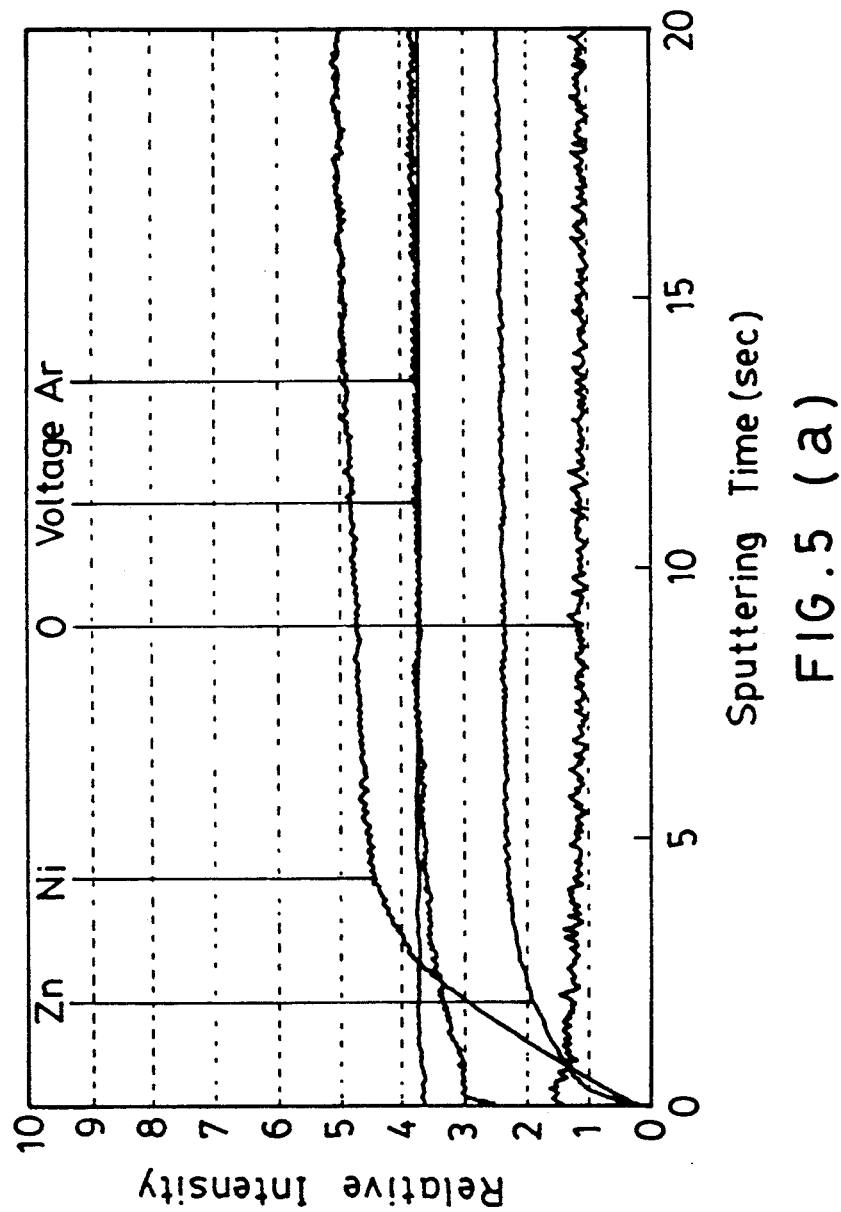

GLOW DISCHARGE ATOMIC EMISSION SPECTROSCOPY AND APPARATUS THEREOF

FIELD OF THE INVENTION

The present invention relates to glow discharge atomic emission spectroscopy (hereinafter referred to as GDS) and the apparatus, in particular, relates to an improved GDS suitable for the analysis of the uppermost surface layer of a specimen in the direction of depth.

The improved GDS and the apparatus according to the present invention can be suitably used for the quick analysis of the uppermost surface layer of a solid specimen in the direction of depth, for example, the surface analysis of steel materials such as cold-rolled steel plates or surface-processed steel plates, the surface analysis of semiconductors or the surface analysis of other metallic or nonmetallic materials.

DESCRIPTION OF RELATED ART

GDS is a method in which a rare gas such as argon gas is introduced into a discharge tube on the order of several tens of Pa (1 atm = $1.013 \times 10^5$ Pa); an abnormal glow discharge is made to occur using a specimen as a cathode; the rare gas elements are ionized to form a discharge plasma; the surface of the specimen is sputtered continuously with the produced ions of the rare gas; the sputtered atoms of the specimen are excited and emit light in a negative glow region in the discharge plasma by inelastic collision with electrons or the rare gas ingredients; the composition of the surface layer of the specimen is qualitatively and quantitatively analyzed by spectroscopically analyzing the atomic emission spectra of the sputtered specimen ingredients.

Among glow discharge tubes which have been used in conventional GDS methods, for example, there is a hollow anode type, such as the one developed by Grimm as shown in FIG. 1 (refer to the Japanese patent gazette 21680/74).

In the discharge tube 1, an opening end of an anode 12 positioned on the opposite side of a specimen 10 is sealed with a fused quartz window 14 and a hollow cathode 16 is fixed to the anode 12 in an electrically insulated and sealed state, and the other opening end is vacuum-sealed in the state where the specimen 10 is closely stuck to the cathode 16. Argon gas flows into a hollow part 32 of the glow discharge tube 1 through an argon gas introduction tube 18 and also the internal pressure of the anode 12 is adjusted by exhausting with a first vacuum pump 20 through a first exhaust pipe 34 to be an optimum pressure for an abnormal glow discharge; on the other hand, a space between an anode pipe 12B and the cathode 16 is exhausted with a second vacuum pump 22 through a second exhaust pipe 36 to produce a state where there is pressure difference between the inside and the outside of the anode pipe 12B, and an abnormal glow discharge is generated. The element analysis of the specimen 10 is made possible by making a spectral analysis of the light generated by the abnormal glow discharge. A symbol 53 is a high voltage power supply for discharge, 42 is a spectroscope, 44 is a detector and 46 is an integrator.

A GDS apparatus using, for example, a Grimm type discharge tube as mentioned in the above has been used for the surface analysis of metal, but the measurement range of it is limited to thick surface layers of more than 1 μm thick, because the GDS apparatus was developed for elemental analysis, and it has been difficult to use it for the analysis of the uppermost surface layers of the thickness in the range of several tens to several hundreds of nm in the direction of depth.

The reason is that in a conventional GDS apparatus the discharge in the range to the depth of about 100 nm from the surface is unstable. The following are considered to be the causes of the above-mentioned phenomenon: (a) the fluctuation of breakdown voltage at the start of discharge, and (b) the rise of a discharge voltage and the decrease of a light emission intensity caused by the sputtering of gas ingredients adsorbed or organic substances such as oil stuck on the surface of the specimen or on the surface of the discharge tube into the inside of the discharge tube during the discharge, which is followed by disassociation reactions of the sputtered ingredients in the light emission plasma subsequent temporary lowering of the plasma temperature.

In order to solve the problem, in a conventional Grimm type discharge tube, an apparatus is proposed in which a third electrode (sub-electrode) is provided in the light emitting portion between an ordinary anode and a specimen as a cathode, and the discharge voltage and the discharge current between the anode and the cathode can be independently and arbitrarily controlled utilizing the third electrode (refer to a Japanese utility model laid open No. 91694/78 and to FIG. 2). Further, a technology is proposed in which by using the above-mentioned apparatus an auxiliary discharge is performed between the anode and the third electrode as a cathode, and besides a preliminary discharge (hereinafter referred to as pre-discharge) is performed in a normal glow discharge region between the anode and a specimen as a cathode (Mr. Ohashi and others, Iron and Steel (Japan), Vol. 69 (1983), No. 10, pp. 1344 to 1349). In these methods, the inside of the discharge tube and the surface of the specimen are made cleaner and also it is made possible to start a main discharge (abnormal glow discharge) more smoothly owing to the effect of the above-mentioned pre-discharge and the auxiliary discharge.

Even when the pre-discharge and the auxiliary discharge are applied, the removal effect of adsorbed substances and extraneous substances on the surfaces of the specimen and the electrodes of the discharge tube is found to be insufficient. For example, if oxygen is contained in the rare gas in the discharge tube originating in the adsorbed gas ingredient, the discharge is not stable and hard to start. Therefore, there still remains a problem in the element analysis in a region to the depth of several tens of nm from the surface of a solid body, for example, it has been difficult to perform a quantitative analysis of elements which are stuck, segregated or concentrated on the metal surface in the depth of several nm to several tens of nm.

SUMMARY OF THE INVENTION

The present invention is invented to solve the above-mentioned problem. The object of the invention is to provide an improved GDS and the apparatus with which the element distribution of the uppermost surface layer of a solid specimen in the direction of depth can be simply and quickly analyzed.

The method according to the present invention is to solve the above-mentioned problem, and it is an improved glow discharge atomic emission spectroscopy which is suitable for the analysis of the uppermost surface layer of a solid specimen comprising the following processes:

(a) an evacuation process of the inside of a glow discharge tube, in which a specimen is fixed to the glow discharge tube and the evacuation is executed making a rare gas flow to prevent the mixing of air;

(b) a process in which after the inside of the discharge tube has reached a constant degree of vacuum, the flow of the rare gas is cut off to keep the inside space at a higher degree of vacuum, and next, the rare gas is introduced again to keep the inside of the discharge tube at the constant degree of vacuum;

(c) a process in which a voltage is applied between a specimen as a cathode and an anode to make a minute current flow between them to perform a pre-discharge (preliminary discharge) in a normal glow discharge region for removing adsorbed or extraneous substances on the surface of the specimen; and (d) a process in which a higher voltage is applied between the specimen as the cathode and the anode to make a constant current flow between them to perform a discharge in an abnormal glow discharge region for performing the analysis of the specimen surface.

In the pre-discharge process (c), as described above, when an auxiliary discharge between the sub-electrode provided in the discharge tube and the anode, and subsequently, a pre-discharge between the sub-electrode and the specimen as the cathode are performed to remove adsorbed or extraneous substances on the surfaces of the specimen and the anode, further improved conditions for the analysis can be obtained.

The above-mentioned constant degree of vacuum and high degree of vacuum can be in the ranges of b 10 to 60 Pa and 1 to 3 Pa respectively.

The minute current in the preliminary discharge can be in the range of 10 nA to 10 mA, for example.

With the apparatus according to the present invention, the method according to the present invention can be properly executed.

The glow discharge atomic emission spectroscopic apparatus comprising a glow discharge tube composed of an anode and a specimen as a cathode, an introduction pipe for introducing a rare gas into the glow discharge tube, a first and a second exhaust pipes for exhausting the inside of the discharge tube, a vacuum gauge, a high voltage power supply to be used for discharge, and a spectroscope, is provided with an electromagnetic valve for adjusting the quantity of a rare gas to be introduced being provided in the introduction pipe; a low current power supply to be used for removing adsorbed or extraneous substances on the surface of the specimen by generating a pre-discharge between the anode and the specimen as the cathode with a specified minute current between them; and a control device for automatically executing the control of the open/close of the electromagnetic valve with the output of the vacuum gauge to maintain the degree of vacuum inside the discharge tube at a constant value or at a higher value, and also for automatically controlling the high voltage power supply to be used for discharge and that of the low voltage power supply.

It is further preferable to provide a DC power supply in place of the low current power supply, and to provide a sub-electrode for generating an auxiliary discharge between the sub-electrode and the anode and a pre-discharge between the sub-electrode and the specimen as the cathode to remove adsorbed or extraneous substances on the surface of the anode and the specimen, and to make it possible to control the ON/OFF of the DC power supply by the control device.

BRIEF DESCRIPTION OF THE DRAWINGS

FIGS. 5(a)-5(c) show an example of GDS measurement on a Zn-Ni plated steel plate specimen.

DETAILED DESCRIPTION OF THE PREFERRED EMBODIMENT

The detailed explanation will be given on the glow discharge atomic emission spectroscopy and the apparatus according to the present invention in the following. Argon gas is used as a rare gas in the apparatus.

Figure 1:
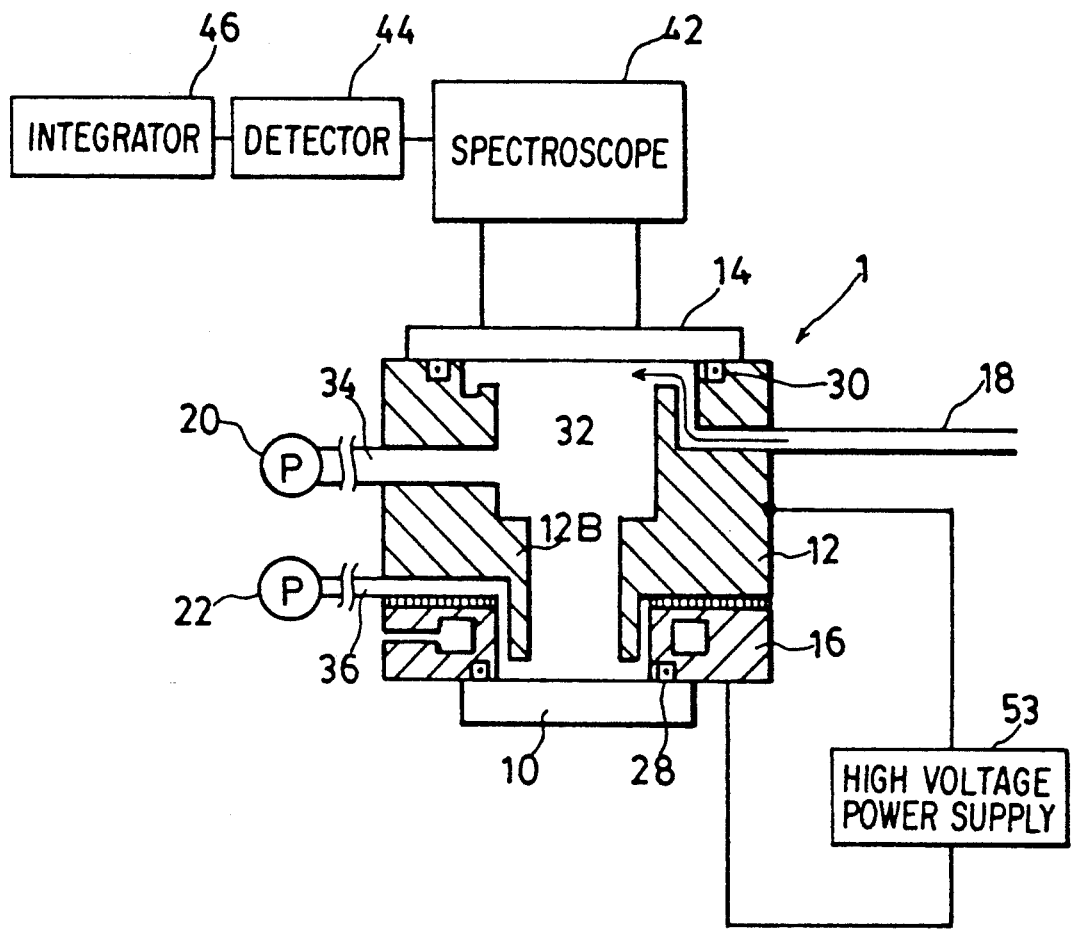
FIG. 1 shows a conventional Grimm type glow discharge tube.
Figure 3:
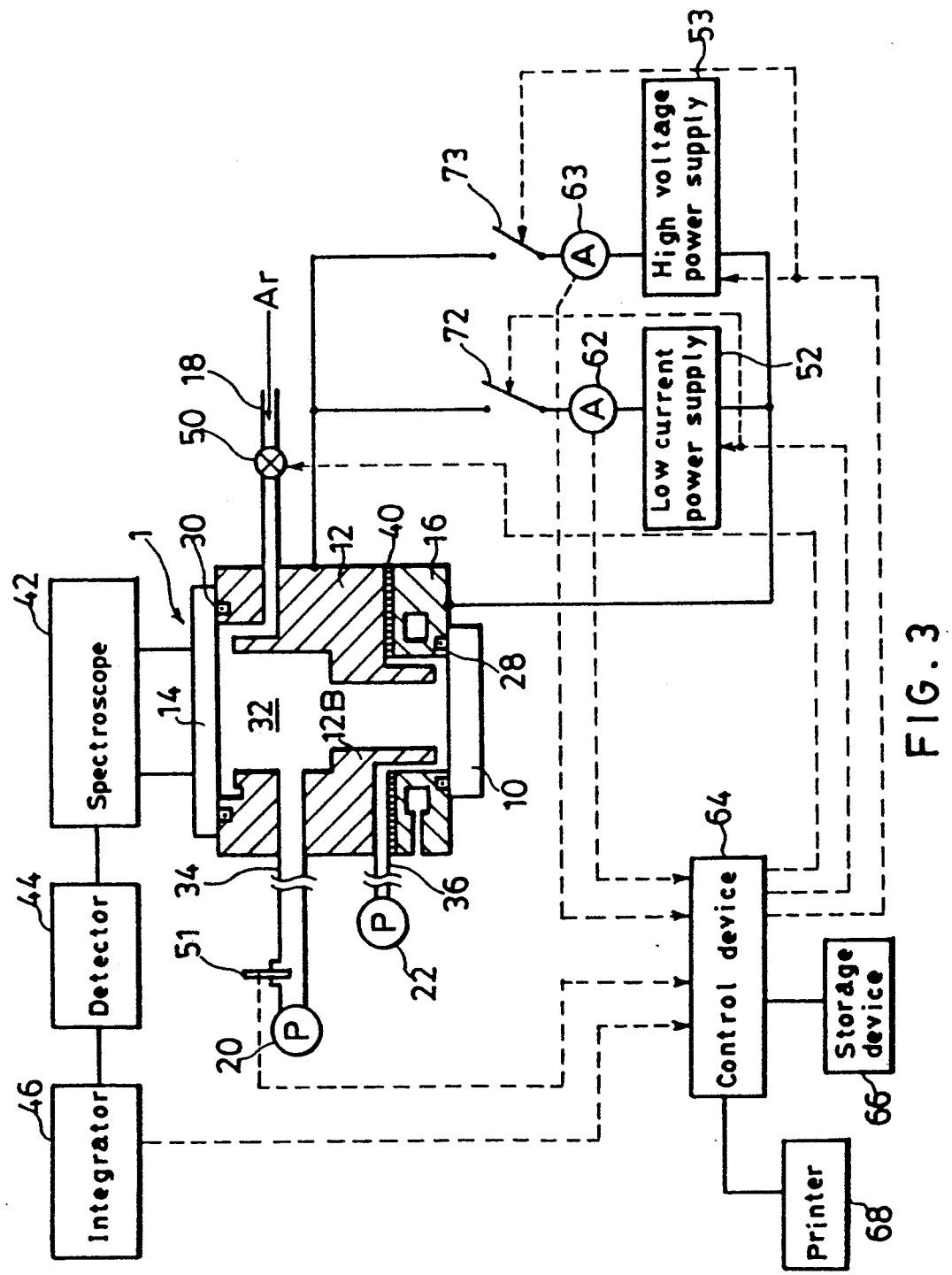
FIG. 3 shows an embodiment of the glow discharge atomic emission spectroscopic apparatus according to the present invention.

FIG. 3 shows an embodiment of the glow discharge atomic emission spectroscopic apparatus according to the present invention, but the present invention is not limited to this. A glow discharge tube in FIG. 3 is a modified conventional glow discharge tube 1 shown in the previously-described FIG. 1, in which an electromagnetic valve 50 is fixed in the argon gas introduction pipe 18 and a vacuum gauge 51 is added to the first exhaust pipe 34.

The constituent elements of the apparatus such as a spectroscope 42 which separates the emitted light by discharge into its spectral components, a detector 44 which detects separated spectral components, an integrator 46 which converts a detected signal into emitted light intensity, and a high voltage power supply 53 to generate a discharge for measurement are similar to those in conventional examples.

Figure 2:
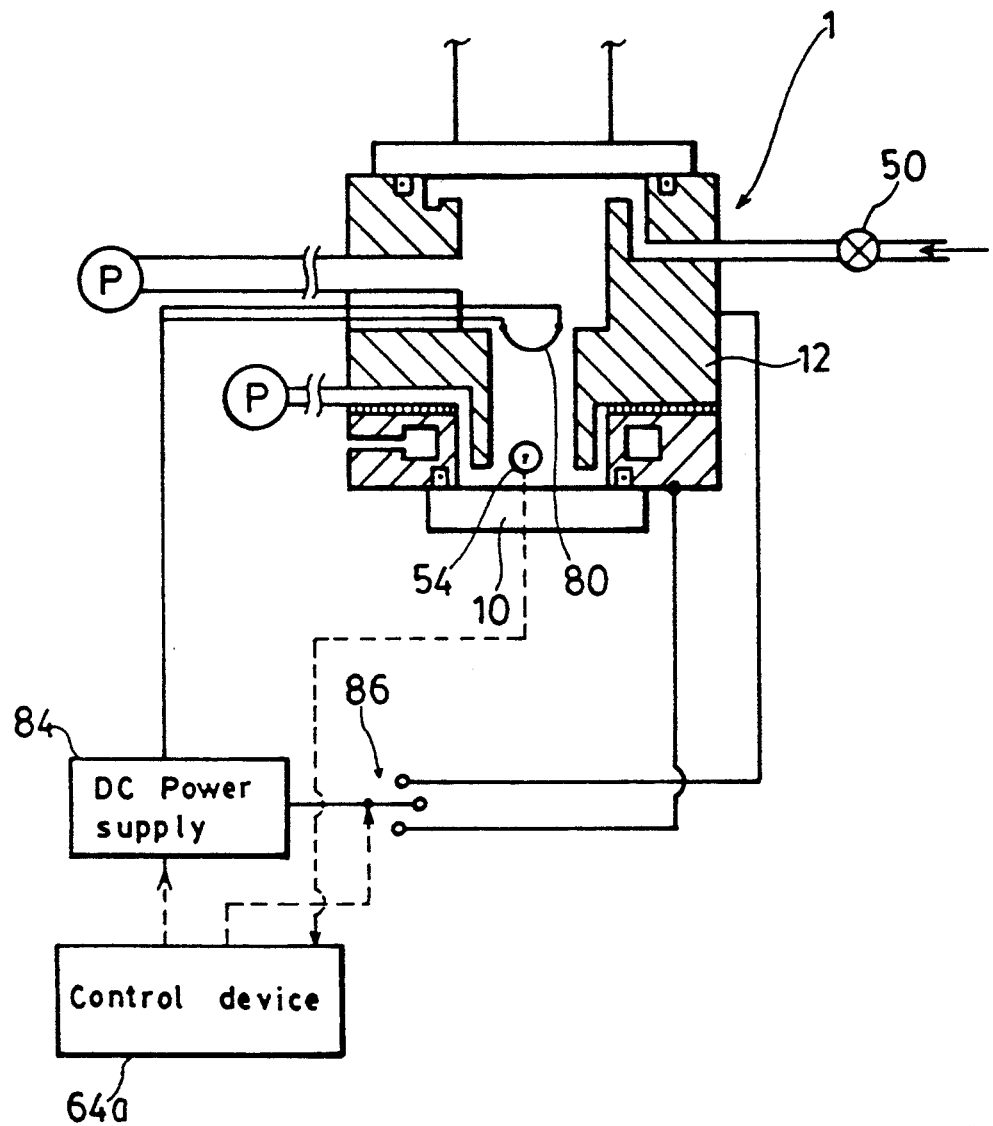
FIG. 2 shows a conventional Grimm type glow discharge tube with a sub-electrode.

Besides those mentioned above, the following are provided: an ammeter 63 for detecting a discharge current; a control device 64 (distinguishable, as will be seen from the discussion to follow, from the control device 64a, shown in FIG. 2) which reads the output from the integrator 46 for obtaining the intensity of the emitted light, and controls the high voltage power supply 53 with a switch 73 and the open/close of the electromagnetic valve 50.

Furthermore in the present invention, to execute a pre-discharge in a normal glow discharge region, a low current power supply 52 to make a minute current flow, a microammeter 62 to detect the minute current and a switch 72 are provided, and also a function of reading the indicated value of the microammeter into the control device 64 to control the low voltage power supply 52 and the switch 72 is provided.

In the GDS apparatus according to the present invention, a specimen 10 is pressed against an O-ring 28 and it is fixed to the glow discharge tube 1 by evacuation. In this case, at the same time air is taken into the discharge tube. In a conventional method, a GDS apparatus is used in a state where argon gas is constantly made to flow for the purpose of limiting the mixing of air to a minimum. The mixing of air into the discharge tube varies corresponding to the environment such as the temperature or the humidity in the surroundings of the apparatus or the roughness on the surface of the specimen, and there is no reproducibility in the mixing quantity of air. According to the present invention, after the evacuation is further continued for a few seconds, the inside of the discharge tube reaches a stationary state at a pressure of 10 to 60 Pa according to the pressure gauge 51. At this degree of vacuum the electromagnetic valve 50 is automatically closed by the control device 64, the introduction of argon gas is suspended (gas-cut) and the inside of the discharge tube is kept at a high degree of vacuum in the range of 1 to 3 Pa for several tens of sec. Then the electromagnetic valve 50 is opened again by the control device 64 to introduce argon gas and the state is kept as it is for several tens of sec. At this time the degree of vacuum inside the discharge tube is in the range of 10 to 60 Pa.

In the next step, the control device 64 controls the power supply 52 to apply a voltage between the specimen 10 as the cathode and the anode 12 by operating the switch 72 to make a constant minute current flow between them. The current flowing at this time is detected by the microammeter 62 to be compared with a discharge current value which is previously set and the voltage of the power supply 52 is automatically adjusted by a feedback mechanism to make the difference between the set discharge current value and the detected current value be zero. At this time the discharge current value is set in the range of 10 nA to 10 mA, for example, and a pre-discharge is performed in the normal glow discharge region.

Next, the control device 64 opens the switch 72 and closes the switch 73, which makes the power supply 53 apply a voltage between the specimen 10 and the anode 12 to make a fixed current flow between them. In this case, the voltage of the power supply 53 is also automatically adjusted. At this time, the discharge current is set in the range of 20 to 60 mA and an abnormal glow discharge is generated; the surface of the cathode specimen 10 is sputtered and the light emission of the constituent elements of the specimen is generated inside the tube and the emitted light is detected through a fused quartz window 14 and the spectroscopic analysis is performed in a similar way to that used in a conventional method.

In the present invention, after the specimen 10 is fixed to the discharge tube 1, the introduction of argon gas is temporarily suspended (gas-cut) and the inside of the discharge tube is kept at a high degree of vacuum, thereby gas ingredients such as oxygen, nitrogen or carbon dioxide introduced by the mixing of air can be removed which are difficult to remove in a state of low degree of vacuum. On the surface of the tube wall gases in the air, such as oxygen, nitrogen and carbon dioxide are adsorbed, but with the lowering of partial pressure of each gas inside the tube the gases come off the tube wall and can be exhausted through vacuum pumps 20 and 22. After that when argon gas is introduced again the partial pressures of oxygen, nitrogen and carbon dioxide inside the tube can be lowered; therefore the partial pressure of argon gas inside the discharge tube 1 can be kept constant without being influenced by the environment, which makes it possible to perform spectroscopic analysis always under stable discharge conditions.

In the case of a pre-discharge in a normal glow discharge region, argon positive ions produced in the discharge tube 1 have not enough energy to sputter the cathode material itself and they act on only gas ingredients adsorbed or organic substances such as oil stuck on the surface of the specimen 10 to remove them from the surface of the specimen, so that the start of a main discharge for the measurement is performed in a state where there is no surface impurity layer. Therefore there is no large fluctuation in the plasma temperature, and even an element segregated or concentrated in a depth of several tens of nm from the surface can be easily detected.

In the present invention, since the open/close of the electromagnetic valve 50 is performed by the control device 64, the introduction or the cut-off of argon gas (gas-cut) is not limited to once only and it is possible to repeat the open/close of the valve a plurality of times or to set the period of open/close of the valve optionally; therefore it is possible to perform the gas-cut several times or to lengthen the period of the open/close of the valve corresponding to the conditions of the surroundings, to the conditions of the specimen surface or to the extent of dirtiness of the anode.

In FIG. 3, the vacuum gauge 51 is disposed in the portion of the first exhaust pipe 34, but the vacuum gauge 51 is not necessarily placed in the portion of the first exhaust pipe 34; for example, it is also possible to place it in the vicinity of the specimen 10 inside the discharge tube 1 for the measurement of the degree of vacuum like the vacuum gauge 54 shown in FIG. 2, so far as the placing does not have an effect on the discharge. In this case, the gas pressure in the vicinity of the specimen surface can be measured, so that it is possible to control the gas partial pressure with higher precision.

In an embodiment according to the present invention as shown in FIG. 3, a pre-discharge is performed between the anode of the discharge tube 1 and the specimen 10 as the cathode, but as shown in FIG. 2 it is also possible to provide a sub-electrode 80 in the discharge tube 1 and a positive voltage is applied to the sub-electrode 80 by providing a DC power supply 84 for applying a positive voltage to perform an auxiliary discharge between the sub-electrode 80 and the anode 12, and a pre-discharge between the sub-electrode 80 and the specimen 10; 86 is a changeover switch for it. By executing the auxiliary discharge and the pre-discharge, the adsorbed or extraneous substances on the surfaces of the anode 12 and the specimen 10 can be removed, which makes it possible to improve further the discharge stability.

As described in detail above, in the apparatus according to the present invention an electromagnetic valve is fixed in the introduction portion of the rare gas introduction pipe, whose open/close is controlled by a control device according to the measurement result of the degree of vacuum inside the first exhaust pipe or at a point being very close to the cathode. Therefore the introduction of a rare gas into the discharge tube can be suspended temporarily (gas-cut), which makes it possible to maintain the inside of the discharge tube evacuated with a vacuum pump at a high degree of vacuum. By the gas-cut, the gases which remain inside the tube such as oxygen, nitrogen and others are taken out to the outside of the tube which are difficult to exhaust in a low degree of vacuum; when the electromagnetic valve is opened again to introduce the rare gas, the oxygen partial pressure etc. becomes low, thereby it is made possible to obtain the rare gas partial pressure corresponding to the quantity of the rare gas inflow. Owing to this, the discharge is stabilized and accurate analysis becomes possible, that is, the preciseness in the measurement by the glow discharge atomic emission spectroscopic method is improved.

In the GDS method according to the present invention, following a gas-cut as a first process, a pre-discharge as a second process is performed right before the execution of the spectroscopic analysis. The pre-discharge is performed with a minute current in the range of 10 nA to 10 mA, for example, between the specimen as the cathode and the anode. It is called a normal glow discharge. In the pre-discharge, rare gas ions having the energy in the order not to generate the sputtering of the specimen itself impinge upon the specimen surface layer and causes a physical phenomenon in which gas ingredients adsorbed on the surface layer or organic substances such as oil stuck on the surface layer are removed. Owing to the pre-discharge, the fluctuation of discharge conditions in the initial period of spectroscopic analysis is removed and the detection of elements segregated or concentrated on the solid specimen surface is made possible; further, the detection of gaseous elements such as O, N and H is made possible; thus the application field is enlarged.

Further in the pre-discharge process, if a sub-electrode is provided inside the discharge tube and an auxiliary discharge is generated between the anode and the sub-electrode, and a pre-discharge is generated between the specimen as the cathode and the sub-electrode, the adsorbed or extraneous substances on the surfaces of the anode and the specimen can be removed further effectively.

Figure 4:
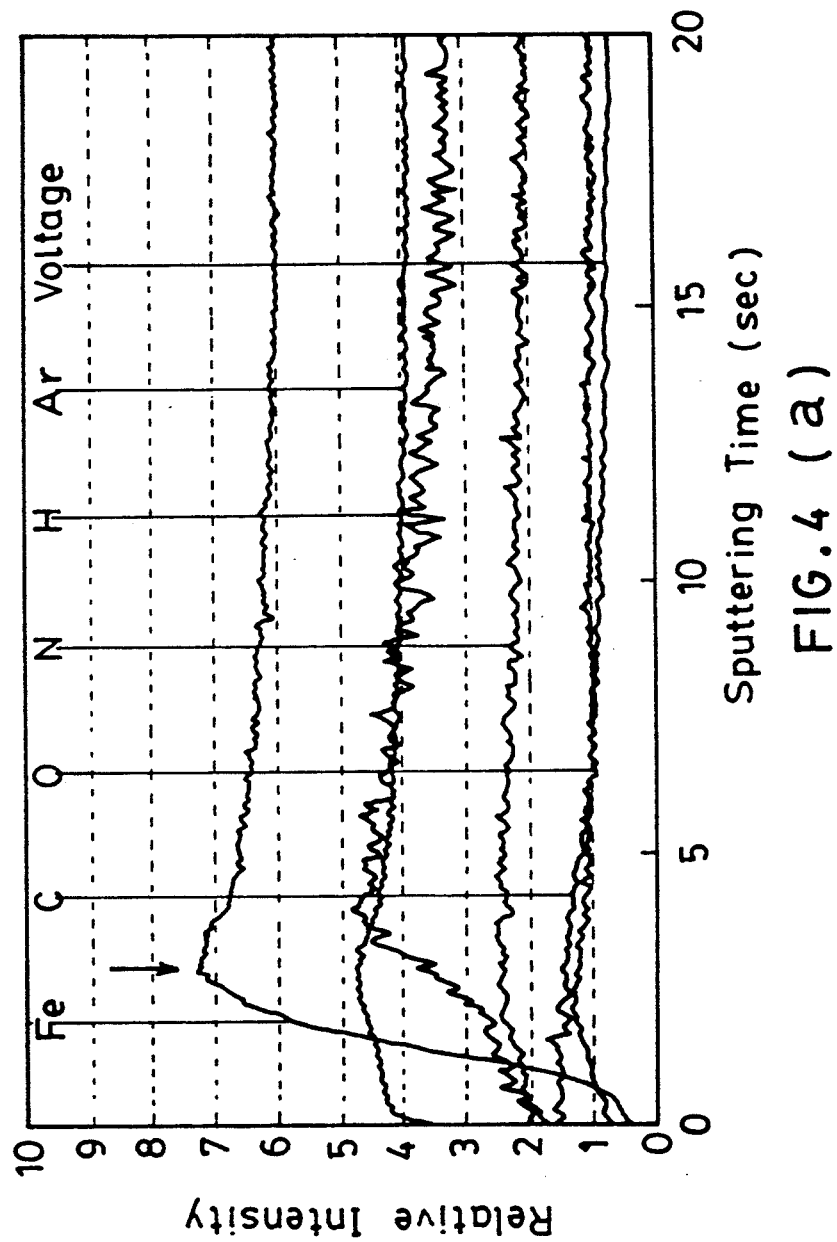
FIGS. 4(a)-4(c) show an example of GDS measurement on a pure iron specimen.
Figure 4:
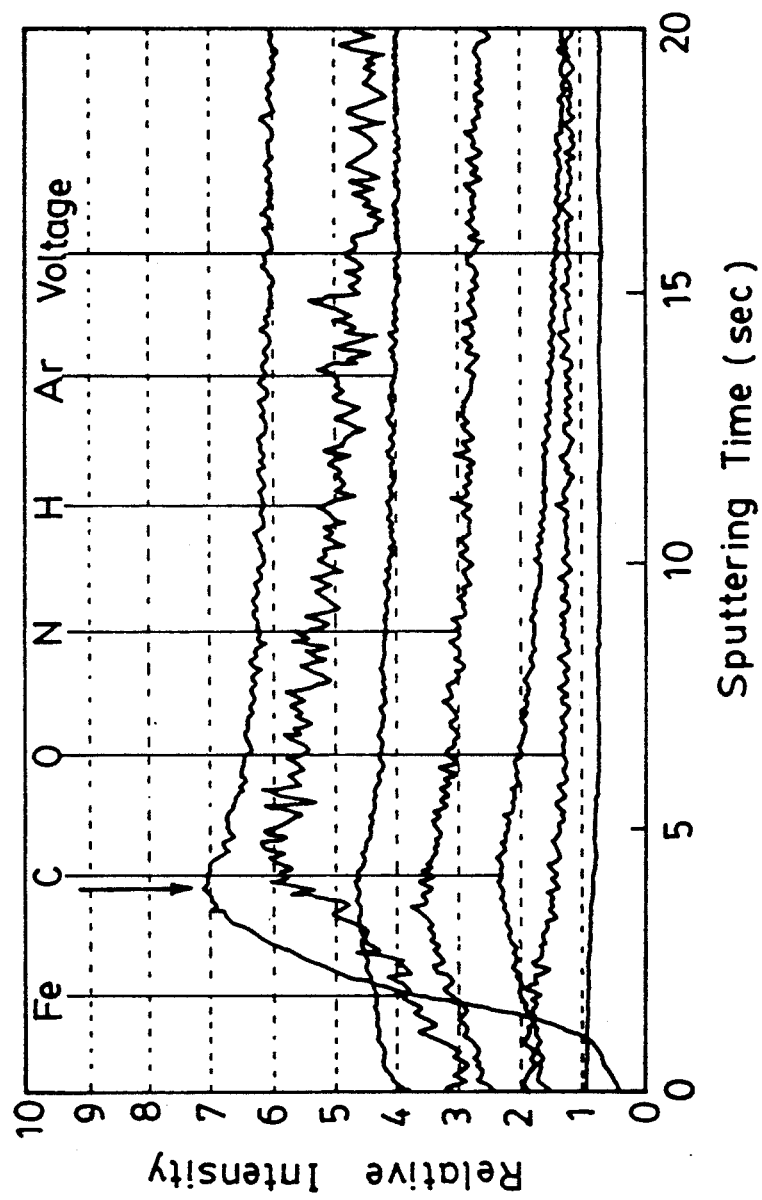
Figure 4:
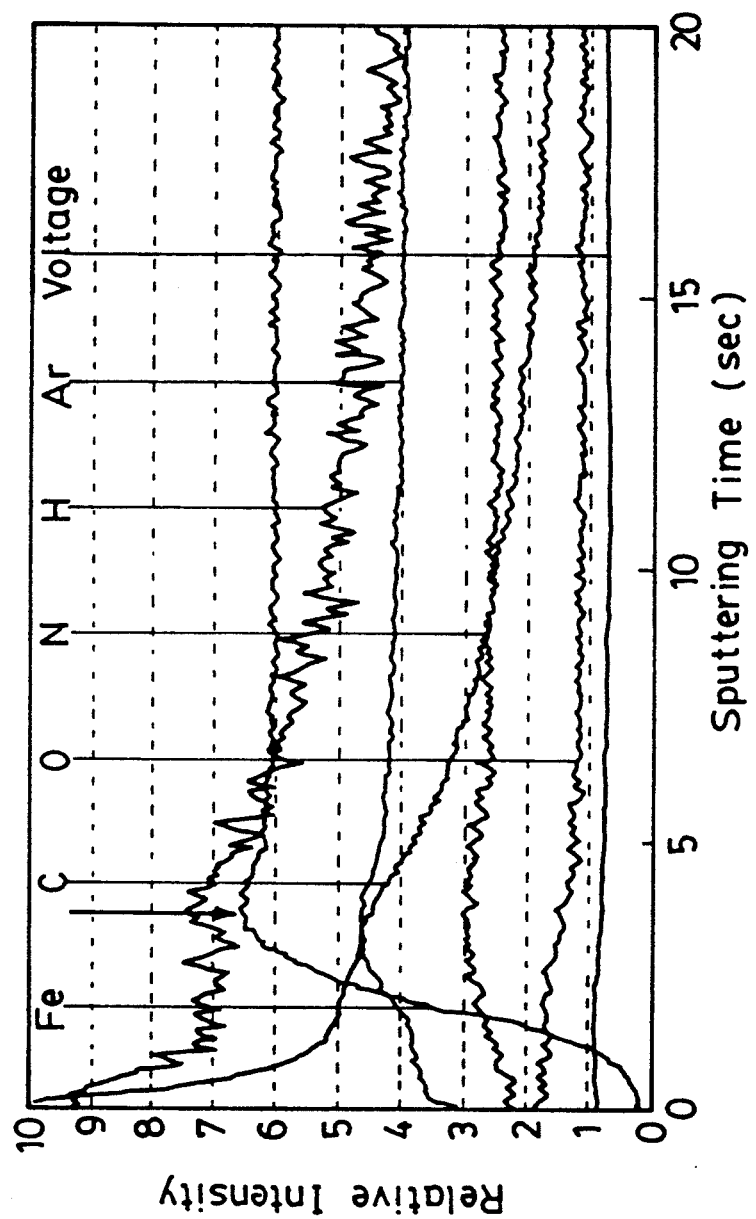

The analyses of uppermost surface layers are performed by a GDS method on two kinds of specimens with a GDS apparatus according to the present invention. The results are shown in FIG. 4 and FIG. 5 respectively.

Figure 5B:
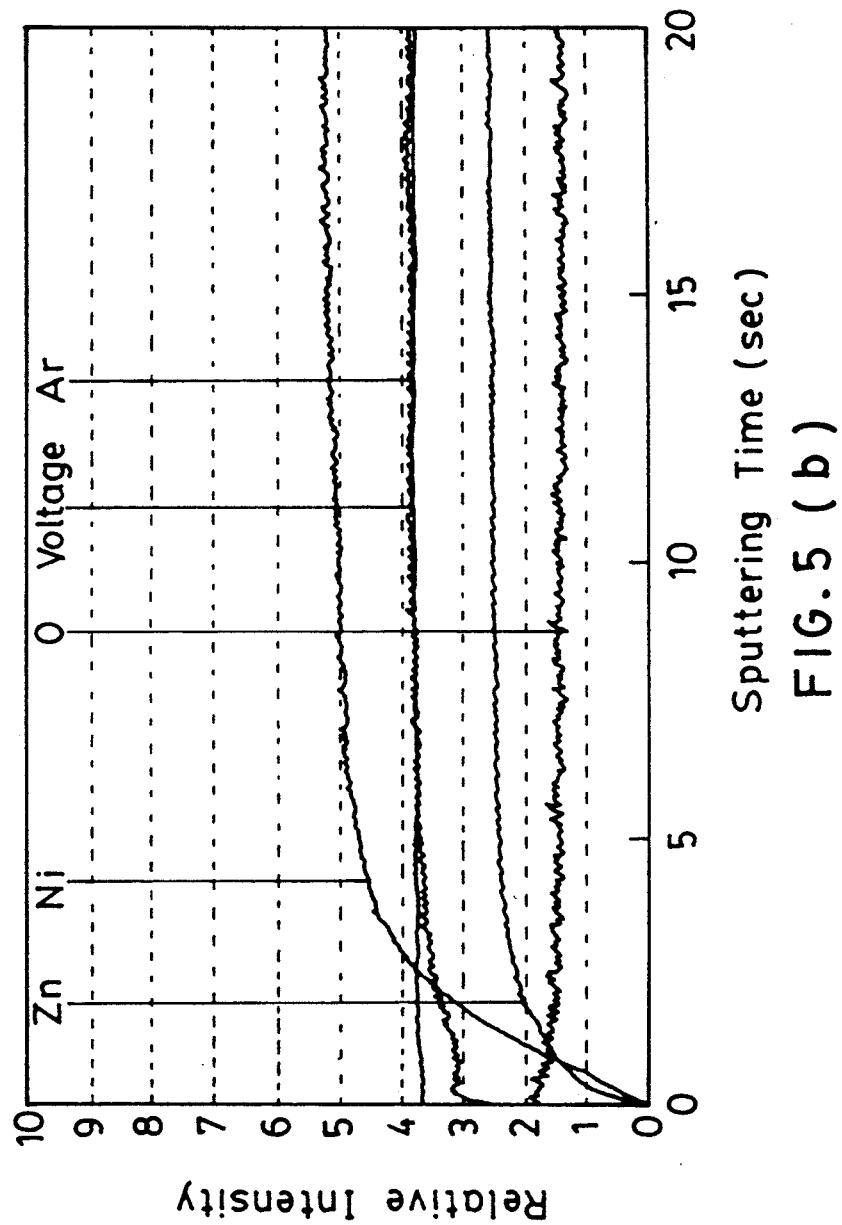
Figure 5C:
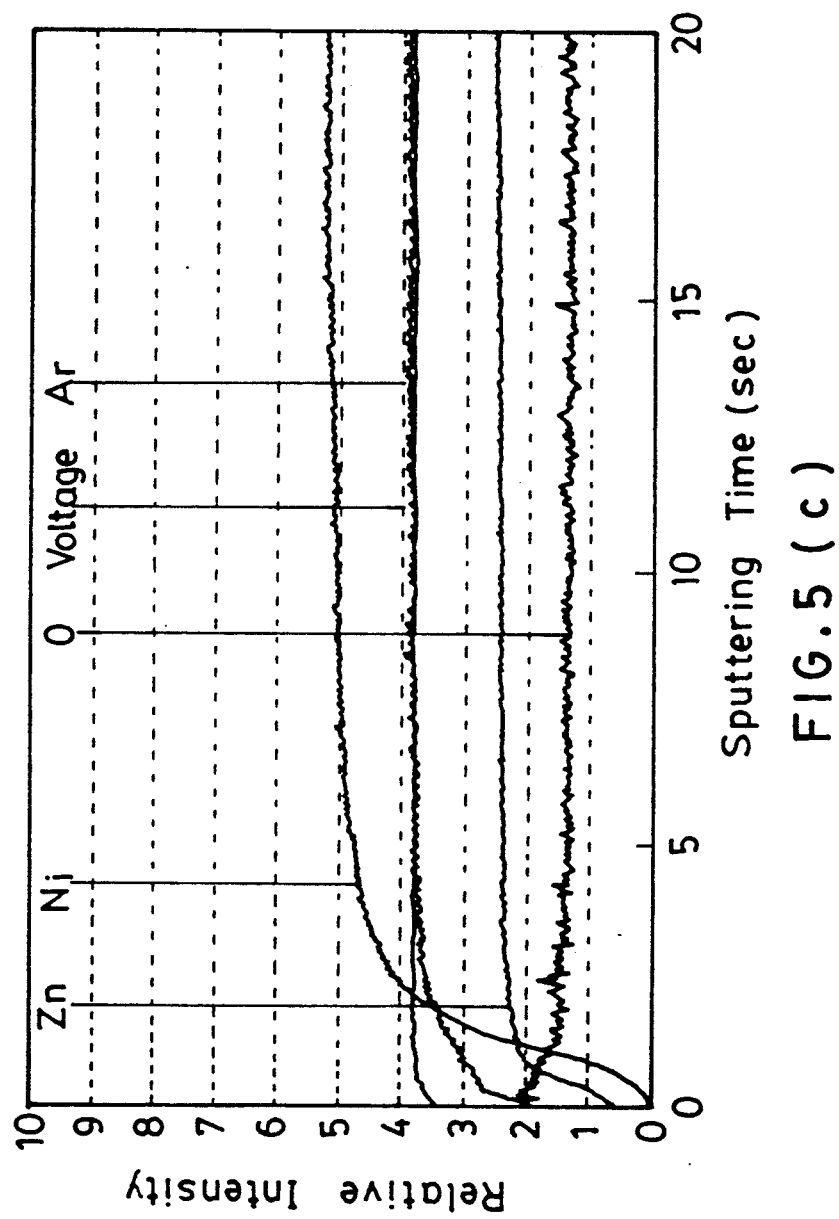

FIG. 4(a) to FIG. 4(c) show the measurement examples on a pure iron specimen, and FIG. 5(a) to FIG. 5(c) show the measurement examples on a Zn-Ni plated steel plate specimen; FIG. 4(a) and FIG. 5(a) correspond to an embodiment, and FIG. 4(b), FIG. 4(c), FIG. 5(b) and FIG. 5(c) correspond to comparison examples.

FIG. 4(a) shows a GDS measurement example of pure iron after a pre-discharge following a single gas-cut.

FIG. 4(b) shows a comparison measurement example by a conventional GDS method of pure iron after a pre-discharge without performing a gas-cut.

FIG. 4(c) shows a comparison measurement example by a GDS method of pure iron after the execution of a gas-cut only.

The relative degrees of vacuum at the time of gas-cut and pre-discharge to the main discharge, as compared are 2.5 Pa and 50 Pa, respectively. The discharge current at the time of the pre-discharge is 2 mA.

The discharge current at the time of GDS measurement of a pure iron specimen shown in FIG. 4(a) to FIG. 4(c) is 10 mA. The sputtering time of 20 sec corresponds to the depth of about 30 nm.

FIG. 5(a) is a GDS measurement example of a Zn-Ni plated steel plate after a pre-discharge following two gas-cuts.

FIG. 5(b) is a comparison measurement example by a conventional GDS method of a Zn-Ni plated steel plate after a pre-discharge without performing a gas-cut.

FIG. 5(c) is a comparison measurement example by a GDS method of a Zn-Ni plated steel plate after the execution of a gas-cut only.

The degrees of vacuum at the times of the single gas cut and the pre-discharge to the main discharge are 2.5 Pa and 50 Pa, respectively. The discharge current at the time of the pre-discharge is 2 mA.

The discharge current at the time of GDS measurement of the Zn-Ni plated steel plate shown in FIG. 5a to FIG. 5(c) is 20 mA. The sputtering time of 20 sec corresponds to the depth of 1120 nm from the surface.

As seen from FIG. 4(a) to FIG. 4(c), in the case where only a gas-cut is performed a lot of C and H remain. When only a pre-discharge is performed, C and H are removed pretty well but the removal of N is not sufficient. According to the present invention, by the combination of the gas-cut and the pre-discharge C, H and N are removed remarkably well, and the period of time when the signal intensity of Fe becomes a maximum is particularly shortened; thereby a remarkable cleaning effect on the uppermost surface layer is acknowledged.

As seen from FIG. 5(a) to FIG. 5(c), in the case where only a gas-cut or a pre-discharge is performed a lot of O remains. According to the present invention, O is removed to a level of $\frac{2}{3}$ by the combination of the pre-discharge and the gas-cut; thereby a remarkable cleaning effect on the uppermost surface layer is acknowledged.

As explained in the above, by the method and the apparatus according to the present invention, the uppermost surface layer of a solid specimen is remarkably clean in comparison with the case of conventional GDS measurement where only a pre-discharge is performed; thereby the element distribution on the uppermost surface layer can be simply and quickly analyzed. For the analysis of the uppermost surface layer of a solid specimen, an ion microprobe mass analysis method (IMMA), an Auger electron spectroscopic method (AES) or a photo-electron spectroscopic method (XPS or ESCA) has been used, but the improved GDS method and the apparatus according to the present invention has high possibility to take the place of these conventional surface analytical methods due to its speed and simplicity. It is anticipated that the improved GDS method will be applied to the surface analysis of semiconductor specimens etc. not only to that of steel specimens.

We claim:

1. An improved glow discharge spectroscopy process suitable for analysis of an uppermost surface of a solid specimen comprising the steps of:
   (a) fixing the specimen to a glow discharge tube and evacuating inside the discharge tube to form a vacuum while flowing a rare gas so as to prevent air from entering the tube;
   (b) after the inside of said discharge tube has reached a fixed degree of vacuum, shielding the flow of the rare gas, maintaining the inside of said discharge tube at a higher degree of vacuum and then introducing the rare gas again to cause the inside of said discharge tube to recover the fixed degree of vacuum;
   (c) applying a voltage between the specimen acting as cathode and an anode, flowing a specified minute current to perform a preliminary discharge in a normal glow discharge area and removing absorbed substances on said surface of the specimen; and
   (d) further applying a voltage to the specimen acting as said cathode and said anode, flowing a specified current to perform a discharge in an abnormal glow discharge area to perform an analysis of the surface of the specimen.

2. An improved glow discharge spectroscopy process according to claim 1, wherein the fixed degree of vacuum in said discharge tube is from 10 to 60 Pa and the high degree of vacuum is from 1 to 3 Pa.

3. An improved glow discharge spectroscopy process suitable for analysis of an uppermost surface of a solid specimen comprising the steps of:
   (a) fixing the specimen to a glow discharge tube and evacuating inside the discharge tube to form a vacuum while flowing a rare gas so as to prevent air from entering the tube;
   (b) after the inside of said discharge tube has reached a fixed degree of vacuum, shielding the flow of the rare gas, maintaining the inside of said discharge tube at a higher degree of vacuum and then introducing the rare gas again to cause the inside of said discharge tube to recover the fixed degree of vacuum;
   (c) arranging an auxiliary electrode within the discharge tube, performing a preliminary discharge between an anode and said auxiliary electrode, subsequently performing an auxiliary discharge between a cathode acting as a specimen and said auxiliary electrode so as to remove absorbed substances on said anode and said specimen surface; and
   (d) applying a voltage to the specimen acting as said cathode and said anode, flowing a specified current, performing a discharge at an abnormal glow discharge area and performing an analysis of the surface of the specimen.

4. An improved glow discharge spectroscopy process according to claim 3, wherein the fixed degree of vacuum in said discharge tube in from 10 to 60 Pa and the high degree of vacuum is from 1 to 3 Pa.

5. An improved glow discharge spectroscopic apparatus comprising: a glow discharge tube provided with an anode and a cathode acting as a specimen, an introduction pipe for introducing a rare gas into said glow discharge tube, first and second exhaust pipes for exhausting the inside of said discharge tube, a high voltage power supply for applying a high voltage between said anode and cathode acting as said specimen and a spectroscope for dividing a glow discharge light generated by applying said high voltage, wherein there is provided an electromagnetic valve arranged in said introduction pipe so as to adjust a feeding amount of rare gas; a low current power supply for applying voltage between said anode and said cathode to cause a preliminary discharge with a predetermined fine current to be performed between both said electrodes and to remove an absorbed substance on the surface of said cathode; a vacuum meter arranged in said first exhaust pipe; and a control device for automatically controlling an opening or closing of said electromagnetic valve in response to an output from said vacuum meter, keeping a degree of vacuum within said discharge tube at one of a normal value and a higher vacuum value, and automatically controlling a change-over supply between said discharge high voltage power supply and said low current power supply.

6. An improved glow discharge spectroscopic apparatus comprising: a glow discharge tube provided with an anode and a cathode acting as a specimen, an introduction pipe for introducing a rare gas into said glow discharge tube, first and second exhaust pipes for exhausting the inside of said discharge tube, a high voltage power supply for applying a high voltage between said anode and cathode acting as said specimen and a spectroscope for dividing a glow discharge light generated by applying said high voltage, wherein an auxiliary electrode is arranged in said discharge tube to perform a preliminary discharge between each of said anode and cathode acting as said specimen and to remove absorbed substances on the surface of said specimen; a DC power supply is arranged to supply an applied voltage between each of said electrodes to one of a part between said auxiliary electrode and said anode, and a part between said auxiliary electrode and the cathode acting as said specimen; and a control device is arranged to control automatically a change-over switch for supplying said DC power to one of said parts.

* * * * *